United States Patent
Daniel

(10) Patent No.: US 11,466,310 B2
(45) Date of Patent: Oct. 11, 2022

(54) DETECTION OF CO-OCCURRING RECEPTOR-CODING NUCLEIC ACID SEGMENTS

(71) Applicant: Akoya Biosciences, Inc., Menlo Park, CA (US)

(72) Inventor: Steven Daniel, Carlsbad, CA (US)

(73) Assignee: Akoya Biosciences, Inc., Menlo Park, CA (US)

(*) Notice: Subject to any disclaimer, the term of this patent is extended or adjusted under 35 U.S.C. 154(b) by 243 days.

(21) Appl. No.: 16/659,509

(22) Filed: Oct. 21, 2019

(65) Prior Publication Data

US 2020/0123597 A1     Apr. 23, 2020

Related U.S. Application Data

(60) Provisional application No. 62/747,785, filed on Oct. 19, 2018.

(51) Int. Cl.
*C12Q 1/6818* (2018.01)
*C07K 14/705* (2006.01)

(52) U.S. Cl.
CPC .......... *C12Q 1/6818* (2013.01); *C07K 14/705* (2013.01); *C12Q 2563/103* (2013.01); *C12Q 2563/107* (2013.01); *C12Q 2565/1015* (2013.01)

(58) Field of Classification Search
CPC .. C12Q 1/6818; C12Q 1/6841; C12Q 1/6869; C07K 14/705
See application file for complete search history.

(56) References Cited

U.S. PATENT DOCUMENTS

| | | | |
|---|---|---|---|
| 6,943,242 B2* | 9/2005 | Samartzidou | C12Q 1/6809 435/6.11 |
| 8,691,510 B2* | 4/2014 | Faham | C12Q 1/6881 435/6.12 |
| 2007/0238099 A1* | 10/2007 | Cohen | C12Q 1/6876 435/6.18 |
| 2014/0057799 A1* | 2/2014 | Johnson | C12Q 1/6888 506/9 |
| 2017/0114406 A1* | 4/2017 | Hansen | G16B 30/10 |

FOREIGN PATENT DOCUMENTS

| WO | WO 2012/048340 | 4/2012 | ............ C12Q 1/68 |
| WO | WO 2015/176162 | 11/2015 | ............ C12Q 1/68 |
| WO | WO 2016/176322 | 11/2016 | ............ C12N 15/10 |
| WO | WO 2017/048614 | 3/2017 | ............ G01N 33/50 |

OTHER PUBLICATIONS

Lee et al, Identifying T Cell Receptors from High-Throughput Sequencing: Dealing with Promiscuity in TCRα and TCRβ Pairing, 2017, PLoS Comput Biol., 13(1): e1005313. pp. 1-25) (Year: 2017).*
International Search Report and the Written Opinion of the International Searching Authority for International Application No. PCT/US2019/057275 dated Feb. 19, 2020.
Howie et al., "High-throughput pairing of T cell receptor α and β sequences", *Science Translational Medicine*, vol. 7, Issue No. 301, 11 pages (Aug. 19, 2015).

* cited by examiner

*Primary Examiner* — Narayan K Bhat
(74) *Attorney, Agent, or Firm* — Fish & Richardson P.C.

(57) ABSTRACT

Methods for identifying co-occurrence of nucleic acid segments in a nucleic acid sample from a specimen including obtaining a nucleic acid sample from a specimen, determining sequences of first and second nucleic acid segments in nucleic acid fragments of the sample to generate a first and second sets of sequences, generating a first and second sets of probes from the first and second sets of sequences, exposing a detection sample to a member of the first set of probes and a member of the second set of probes, performing a hybridization analysis to determine whether the members of the first and second sets of probes hybridize to the detection sample, and determining whether the first and second nucleic acid segments co-occur in a common cell of the specimen.

33 Claims, 4 Drawing Sheets

Specification includes a Sequence Listing.

| CDR3 Sequence | Clone Frequency |
|---|---|
| SEQ ID NO 1: TGTGCCAGCAGCCCGGCGACTAGCGGGAGAATCATCGATGAGCAGTTCTTC | 0.252525252525 |
| SEQ ID NO 2: TGTGCTACCCAACTTCTGAGGGAATTGAGCTCCTACAATGAGCAGTTCTTC | 0.232323232323 |
| SEQ ID NO 3: TGTGCCAGTAGTACCCCCCTACTAGAGCGGGAGAGGTACACCGGGGAGCTGTTTTT | 0.151515151515 |
| SEQ ID NO 4: TGTGCCAGCAGCCTGGAGGGGATCACCCCTCCACTTT | 0.151515151515 |
| SEQ ID NO 5: TGCAGTGCTAGGTTTCAGGCAAATCAGCCCCAGCATTT | 0.101010101010 |
| SEQ ID NO 6: TGTGCCAGCGGGCGGCACGGTTGTTTCATATATTT | 0.090909090909 |
| SEQ ID NO 7: TGTGCCAGCAGGCAGCCTGGAGAGGATCACCCCTCCACTTT | 0.010101010101 |
| SEQ ID NO 8: TGAGTGCTAGGTTTCAGGCAAATCAGCCCCAGCATTT | 0.010101010101 |

FIG. 2

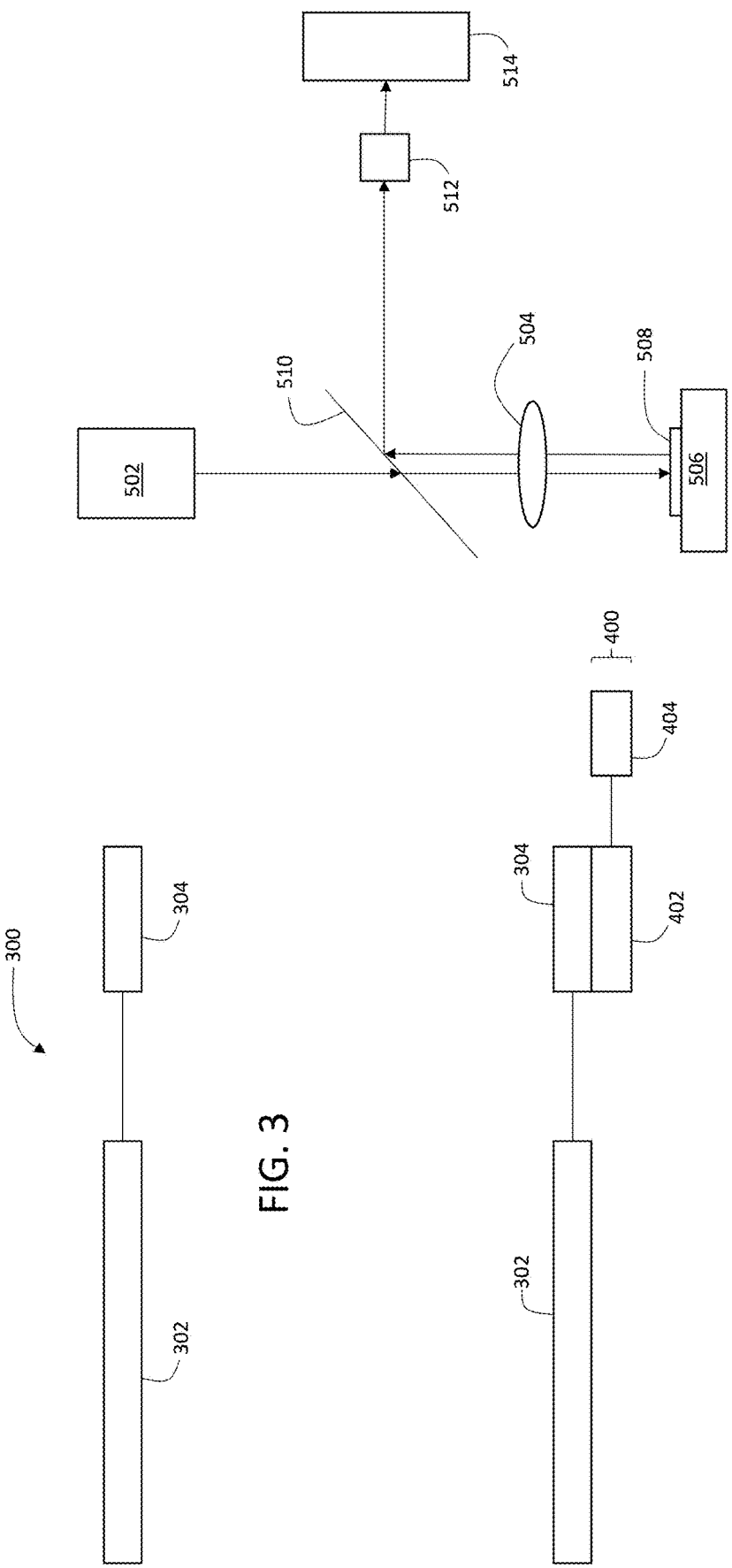

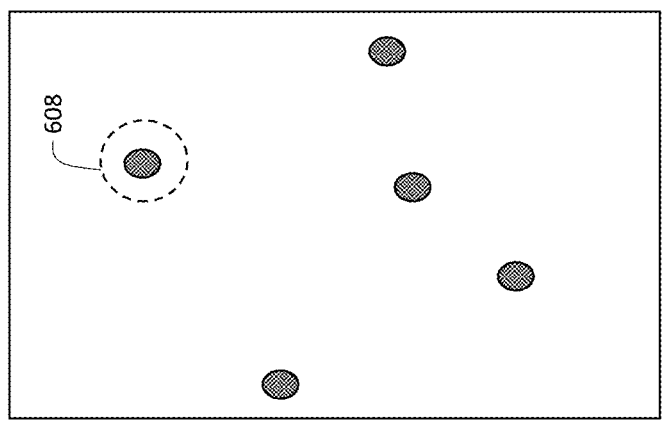
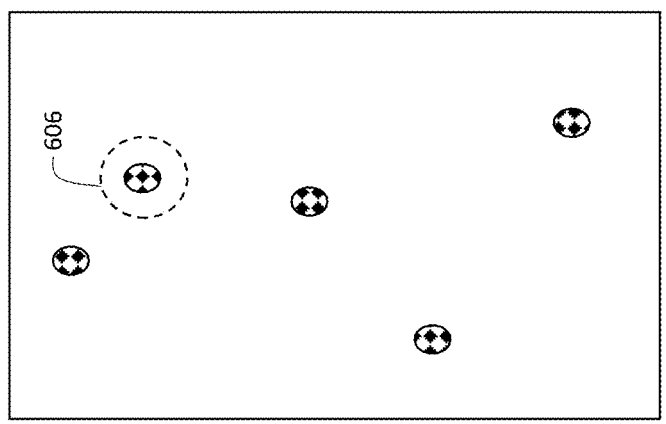
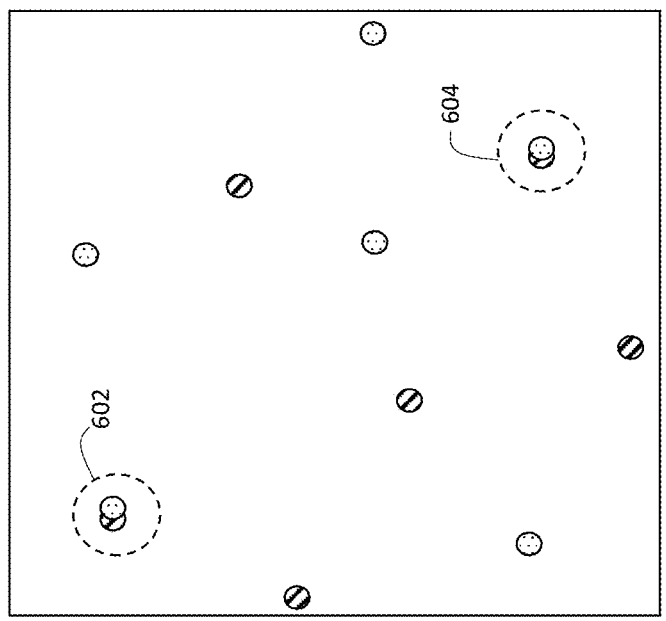
FIG. 6B
FIG. 6A

DETECTION OF CO-OCCURRING RECEPTOR-CODING NUCLEIC ACID SEGMENTS

CROSS-REFERENCE TO RELATED APPLICATIONS

This application claims priority to U.S. Provisional Patent Application No. 62/747,785, filed on Oct. 19, 2018, the entire contents of which are incorporated herein by reference.

SEQUENCE LISTING

A sequence listing, submitted separately as a computer-readable ASCII text file, is part of this disclosure. The sequence listing is named "Sequence_Listing.txt", was created on May 12, 2022, and is 1437 bytes in size. The entire contents of the sequence listing are incorporated by reference herein.

TECHNICAL FIELD

This disclosure relates to the detection of co-occurring of nucleic acid segments, such as coding segments of cell surface receptors.

BACKGROUND

Neoantigen-specific T-cells direct the anti-tumor immune response in tissue, and in turn, neoantigen specificity is mediated through surface-expressed T-cell receptors. T-cell receptors are heterodimers consisting of alpha and beta subunit pairs. Techniques exist for sequencing nucleic acid segments that code for both subunit pairs. However, identifying co-occurring pairs of coding segments from among a population of fragments extracted from a tissue sample remains a challenging problem.

SUMMARY

The present disclosure features methods for identifying co-occurring nucleic acid segments in a sample. The segment sequences can be used for the engineering of T-cells that express neoantigen-specific T-cell receptors, which are then infused into a patient for therapeutic applications. The methods can be used with a wide variety of samples, including fresh and fresh-frozen tissue sections, formalin-fixed, paraffin-embedded (FFPE) tissue sections, and substrate-mounted smears (e.g., blood-derived white blood cells such as peripheral blood mononuclear cells). Probes derived from a first sample or a first portion of a sample are hybridized to a second sample or a second portion of the sample, and detection of specific hybridization events associated with probes related to specific segment sequences is used to determine pairs of co-occurring segments.

In one aspect, the disclosure features methods for identifying co-occurrence of nucleic acid segments in a nucleic acid sample from a specimen, the methods including: obtaining a nucleic acid sample from a specimen, where the nucleic acid sample features a plurality of nucleic acid fragments associated with expression of an antigen receptor molecule in the specimen; determining sequences of first and second nucleic acid segments in the nucleic acid fragments of the sample to generate a first set of sequences corresponding to the first nucleic acid segment and a second set of sequences corresponding to the second nucleic acid in the sample; generating a first set of probes from the first set of sequences, where each member of the first set of probes features an oligonucleotide corresponding to a different one of the first set of sequences linked to a detection moiety; generating a second set of probes from the second set of sequences, where each member of the second set of probes features an oligonucleotide corresponding to a different one of the second set of sequences linked to a detection moiety; exposing a detection sample obtained from the specimen to a member of the first set of probes and a member of the second set of probes; performing a hybridization analysis to determine whether the member of the first set of probes hybridizes to the detection sample, and to determine whether the member of the second set of probes hybridizes to the detection sample; and determining whether the first and second nucleic acid segments co-occur in a common cell of the specimen.

Embodiments of the methods can include any one or more of the following features.

The antigen receptor molecule can be a T-cell antigen receptor molecule. The first nucleic acid segment can be associated with an α-chain of the T-cell antigen receptor molecule, and the second nucleic acid segment can be associated with a ß-chain of the T-cell antigen receptor molecule.

The antigen receptor molecule can be a B-cell antigen receptor molecule. The first nucleic acid segment can be associated with a heavy chain of the B-cell antigen receptor molecule, and the second nucleic acid segment can be associated with a light chain of the B-cell antigen receptor molecule.

The first and second nucleic acid segments can be located in a complementarity determining region 3 (CDR3) portion of the nucleic acid fragments.

The nucleic acid sample can include genomic DNA. The nucleic acid sample can include total RNA. The nucleic acid sample can include nucleic acid molecules from tumor infiltrating lymphocytes.

The specimen can include a fresh or frozen tumor tissue specimen. Obtaining the nucleic acid sample from the specimen can include fixing and embedding the specimen in paraffin, excising a portion of the specimen, and extracting the nucleic acid sample from the excised portion of the specimen. The excised portion of the specimen can include target immune cells. The target immune cells can include tumor infiltrating lymphocytes.

The sequences of the first and second nucleic acid segments can each include between 50 and 200 base pairs (e.g., between 75 and 150 base pairs). The first and second sets of sequences can each include at least 20 different sequences (e.g., at least 50 different sequences).

The first set of sequences can include N different sequences, and generating the first set of probes can include, for each sequence of M of the different sequences that are expressed in highest abundance in the nucleic acid sample, generating a population of oligonucleotides corresponding to the sequence, and linking each member of the population of oligonucleotides to a detection moiety. M can be equal to N or less than N. M can be 48 or less (e.g., 24 or less).

The oligonucleotides of the population can include DNA sequences. The DNA sequences can be complementary to the M different sequences. The oligonucleotides of the population can include RNA sequences. The RNA sequences can be antisense RNA sequences. The antisense RNA sequences can be complementary to RNA transcript sequences corresponding to the M different sequences.

The oligonucleotides of the population can include modified nucleic acids. The modified nucleic acids can include peptide nucleic acids.

The detection moiety can include biotin or a derivative thereof. The detection moiety can include a hapten. The detection moiety can include a fluorescent moiety. The detection moiety can include at least one chelated metal ion. The detection moiety can include a reactive moiety that reacts with an agent to generate chemiluminescence. The detection moiety can include a molecular barcode. The molecular barcode can include an oligonucleotide. Each member of the population can be linked to a common detection moiety that includes the same molecular barcode.

Among the populations of nucleotides corresponding to the M different sequences, the common detection moiety can be unique to one population of oligonucleotides corresponding to only one of the M different sequences. The oligonucleotide can include a DNA sequence, and the DNA sequence can be linked to a 3' end of the member of the population of oligonucleotides.

The detection sample can include a tissue section. The tissue section can include a formalin fixed, paraffin embedded tissue section. The detection sample can include a remaining portion of the specimen following extraction of a portion of the specimen to obtain the nucleic acid sample. The detection sample can include a smear of white blood cells. The white blood cells can include peripheral blood mononuclear cells (PBMCs).

Exposing the detection sample to the members of the first and second sets of probes can include contacting the detection sample with a composition featuring all members of the first and second sets of probes, and removing members of the first and second sets of probes that do not hybridize to the detection sample from contact with the detection sample.

The first set of probes can include J different types of probes, each of the J different types of probes corresponding to one of the first set of sequences, the second set of probes can include K different types of probes, each of the K different types of probes corresponding to one of the second set of sequences, each member of the first and second sets of probes can correspond to only one of the J different types of probes or to only one of the K different types of probes, each member of the first and second sets of probes includes a detection moiety featuring a molecular barcode that is unique to only one type of probe among the J and K different types of probes, and the molecular barcode can include an oligonucleotide.

Performing the hybridization analysis can include: (a) exposing the detection sample to a set of detection probes, each member of the set of detection probes featuring an oligonucleotide sequence that hybridizes to a single type of molecular barcode, and a fluorescent moiety linked to the oligonucleotide sequence; (b) detecting fluorescence emission from members of the set of detection probes hybridized to molecular barcodes in the detection sample; (c) removing from the detection sample the detection probes that are hybridized to molecular barcodes in the sample; and (d) repeating steps (a)-(c) with additional sets of detection probes.

The first set of probes can include J different types of probes, each of the J different types of probes corresponding to one of the first set of sequences, the second set of probes can include K different types of probes, each of the K different types of probes corresponding to one of the second set of sequences, and exposing the detection sample to the members of the first and second sets of probes can include contacting the detection sample with a composition featuring one of the J different types of probes and one of the K different types of probes, and removing from contact with the detection sample any probes of the composition that do not hybridize to the detection sample. Performing the hybridization analysis can include detecting the detection moiety linked to the one of the J different types of probes and detecting the detection moiety linked to the one of the K different types of probes.

The detection moiety linked to the one of the J different types of probes can include biotin or a derivative thereof, and detecting the detection moiety can include binding the detection moiety to a detection probe, the detection probe featuring a moiety that binds to biotin or a derivative thereof and a fluorescent moiety, and detecting fluorescence emission from the fluorescent moiety following binding of the detection moiety to the detection probe. The moiety that binds to biotin or a derivative thereof can include at least one of avidin and streptavidin.

The detection moiety linked to the one of the J different types of probes can include a hapten, and detecting the detection moiety can include binding the detection moiety to a detection probe, the detection probe featuring a moiety that binds to the hapten and a fluorescent moiety, and detecting fluorescence emission from the fluorescent moiety following binding of the detection moiety to the detection probe. The moiety that binds to the hapten can include at least one member selected from the group consisting of a protein, a polypeptide, a polysaccharide, or a liposome.

The detection moiety linked to the one of the J different types of probes can include a fluorescent moiety, and detecting the detection moiety can include detecting fluorescence emission from the fluorescent moiety.

The detection moiety linked to the one of the J different types of probes can include at least one chelated metal ion, and detecting the detection moiety can include liberating the chelated metal ion from the detection moiety, and detecting the liberated metal ion by mass spectrometry.

The detection moiety linked to the one of the J different types of probes can include a reactive group, and detecting the detection moiety can include exposing the reactive group to an agent that reacts with the reactive group to generate chemiluminescence emission, and detecting the chemiluminescence emission following the reaction.

Embodiments of the methods can also include any of the other features described herein, and can include combinations of any features, including those described in connection with different embodiments, except as expressly stated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 2 is a table showing example CDR3 sequences for a particular nucleic acid segment derived from nucleic acid fragments extracted from a sample.

FIG. 3 is a schematic diagram of a nucleic acid segment probe.

FIG. 4 is a schematic diagram of a detection probe.

FIG. 5 is a schematic diagram of a system for obtaining fluorescence and chemiluminescence images indicating hybridization of nucleic acid segment probes in a sample.

FIG. 6A is a schematic fluorescence image showing fluorescence emission corresponding to co-occurring nucleic acid segments in two sample cells.

FIG. 6B is a set of two schematic fluorescence images showing fluorescence emission corresponding to the occurrence of different nucleic acid segments in a sample.

Like reference symbols in the various drawings indicate like elements.

DETAILED DESCRIPTION

Figure 1:
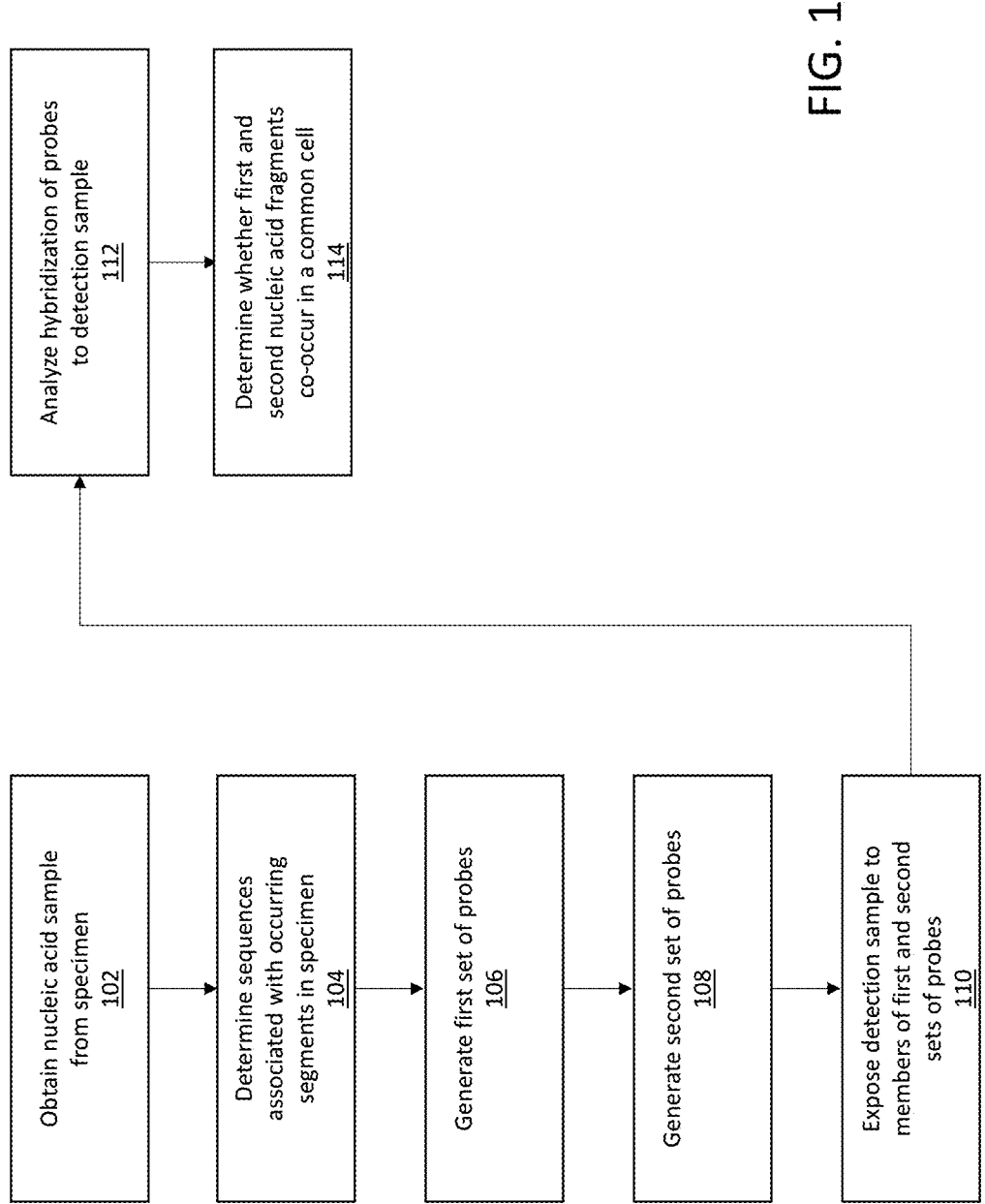
FIG. 1 is a flow chart showing a series of example steps for identifying co-occurrence of nucleic acid segments in a sample.

Chimeric antigen receptor (CAR) T-cell immunotherapies are available to treat a variety of immune diseases, and are readily applied to cancers in which circulating T-cells are extracted from a patient's blood. The extracted T-cells can be re-engineered for surface expression of CAR, replicated in large numbers for dosing, and infused into the patient to specifically target tumor cells. Commercial therapies exist, particularly for lymphomas, and target surface antigens such as CD19 which are common in heme malignancies.

Therapies targeting solid tumors have been more challenging to develop, in part because the cells of such tumors typically express fewer surface markers. However, neoantigens are generated in such tumors through somatic mutations, and may be expressed on the surface of solid tumor cells. Neoantigen specific T-cells direct the patient's immune anti-tumor response. Accordingly, a promising approach to immunotherapies for solid tumors involves re-engineering of T-cells to express surface antigen receptors that interact with a patient's neoantigens. Cloning of re-engineered T-cells and infusion into the patient may yield therapeutic outcomes that are more effective than other, more conventional treatments.

Neoantigen specificity is mediated through T-cell receptors, which are heterodimers consisting of alpha (a) and beta (B) subunit pairs. Commercial methods exist to determine nucleic acid sequences that code specifically for a and B chain fragments in T-cell receptors. However, for a sample extracted from tumor tissue and containing a large number of a and B chain coding nucleic acid fragments, sequencing leads to a distribution of coding sequences for both chain fragments, with no indication of which pairs of coding sequences (i.e., a and B coding sequence pairs) yield functional T-cell receptors.

Identification of T-cell receptors with anti-tumor functionality is a prerequisite to engineered T-cell therapies. By sequencing nucleic acids extracted from such samples and identifying co-occurring nucleic acid coding segments for a and 13 receptor chain fragments among the populations of both a and 13 coding segments, specific functional T-cell receptors can be identified. The co-occurrence information for specific a and 13 coding segments can then be used to engineer populations of T-cells with functional neoantigen receptors, and therefore, anti-tumor functionality.

Next-generation sequencing methods can readily be used to obtain T-cell receptor a and B coding sequences. However, identifying which of tens or hundreds of a coding segments obtained from a typical sample functionally pairs with which of tens or hundreds of B coding segments obtained from the same sample remains a challenging problem. In addition, certain existing analytical methods are not well adapted for use with solid tumor tissues, and in particular, formalin-fixed, paraffin-embedded samples, which is the preferred clinical format for most tumor specimens.

This disclosure features methods for identifying the co-occurrence of nucleic acid segments in a biological sample. The methods can be used with a wide variety of different samples, including tissue sections and blood smears. Sample-specific probes are generated from nucleic acids extracted from the sample, and the probes are hybridized to the sample serially or in parallel. Detection of hybridization events associated with particular, individual probes provides information about which nucleic acid segments are present in the sample, and therefore, which polypeptide chain fragments are co-expressed in the sample. Where the polypeptide chain fragments are paired chain fragments corresponding to a functional receptor, the co-expression information leads directly to identification of functional receptors in the sample.

As described above, an important application of the methods described above is in providing engineered T-cell therapies targeting solid tumors. For such applications, the methods described herein can be applied to the identification of co-occurring nucleic acid segments that code for co-expressed a and 13 chain fragments of functional T-cell neoantigen receptors in a sample. The discussion that follows describes such applications in detail to provide an illustrative example of the methods.

However, the methods described herein are not limited to co-occurrence analysis of nucleic acid segments that code for a and B chain fragments of T-cells. To the contrary, the methods can be used for co-occurrence analysis of nucleic acid segments that code for a variety of polypeptides (or fragments thereof) in many different types of cells and samples. In some embodiments, for example, the methods can be applied to determine co-occurrence of nucleic acid segments that code for other polypeptides in T-cells, including other chain fragments.

In certain embodiments, the methods can be applied to determine co-occurrence of nucleic acid segments that code for polypeptides or fragments thereof in other types of cells. As an example, B-cells can be engineered to provide immunoglobulin therapies, provided that functional B-cells can be identified. B-cells contain paired heavy and light chain fragments, and identifying which B-cells are functional for purposes of engineering and cloning B-cells for therapeutic purposes effectively involves determining co-occurring nucleic acid segments in a sample that code for the heavy and light chain fragments. With this information, B-cells that contain the co-occurring nucleic acid segments can be engineered, and will exhibit therapeutic efficacy.

Similarly, B-cells expressing a specific antigen-specific antibody protein can be used to mass produce the antibody in sufficient quantities that the antibody can be used delivered as a therapeutic, or it can be linked to a separate therapeutic moiety, which can be a small molecule or another therapeutic immune cell that is used to target that moiety to a tumor or other cell type of interest.

FIG. 1 is a flow chart 100 showing a set of example steps (e.g., a workflow) for identifying co-occurrence of nucleic acid segments. In a first step 102, a nucleic acid sample is obtained from a specimen. The specimen is typically a tissue sample removed from an organism, e.g., by biopsy. A suitable specimen can be obtained from a wide variety of organisms, and can for example be a human specimen, or a specimen removed from any other mammalian or non-mammalian organism, including a mouse, a rat, an avian organism, and a simian organism.

Specimens can generally be of various types. In some embodiments, for example, the specimen is a fresh sample of tissue. In certain embodiments, the specimen is a fresh-frozen tissue sample. The specimen can also be a tissue that is fixed in formalin (or another fixative), embedded in a structural medium, and then sectioned (e.g., in a microtome) to form a tissue section (e.g., a formalin-fixed, paraffin-embedded (FFPE)) tissue section.

The specimen can be derived from any of a variety of different types of tissue. In some embodiments, for example, the specimen is extracted from tumor tissue in a patient. The tumor can be a solid tumor, accessed via biopsy or dissection during a surgical or post-surgical operation.

In certain embodiments, the specimen corresponds to one or more cells circulating in a body fluid. For example, the specimen can include one or more white blood cells derived from a patient blood sample. Suitable white blood cells include, but are not limited to, peripheral blood mononuclear cells (PBMCs), for example.

After a suitable specimen has been obtained, a nucleic acid sample is extracted from the specimen. In some embodiments, for example, where the specimen is a tissue section, the specimen can be stained with one or more chromogenic stains and imaged to identify different portions of the specimen. For a specimen that includes tumor tissue, chromogenic staining can be used to reveal tumor margins and identify cells suitable for nucleic acid extraction. More generally, any of a variety of techniques can be used to identify cells in the specimen that are suitable for nucleic acid extraction.

Once a suitable cell (or cells) have been identified, the cell (or cells) is/are isolated from the specimen, and nucleic acids from the cell (or cells) are extracted. Various techniques can be used to isolate a cell or cells from a specimen. For example, in some embodiments, one or more cells are isolated from the specimen using laser capture microdissection. Methods for performing laser capture microdissection are disclosed, for example, in Emmert-Buck et al., *Science* 274: 998-1001 (1996), and in Espina et al., *Expert Rev. Mol. Diagn.* 7(5): 647-657 (2007), the entire contents of each of which are incorporated by reference herein.

Various types of cells (e.g., target immune cells) can be isolated from the specimen for nucleic acid extraction. In certain embodiments, for example, the isolated cells are tumor-infiltrating lymphocytes, which are functional lymphocytes that are responsible for the immune response to tumor cells in the specimen.

Next, a nucleic acid sample is extracted from one of the isolated cells. Nucleic acid extraction can be performed using a variety of methods, depending upon the nature of the nucleic acid. For extraction of DNA, techniques such as cesium chloride gradient centrifugation and solid phase extraction can be used. Suitable examples of such methods include, but are not limited to, those described in Ali et al., *Biomed. Res. Int.* 2017: 9306564 (2017), the entire contents of which are incorporated herein by reference. For extraction of RNA, techniques such as guanidium thiocyanate-phenol-chloroform extraction can be used. Examples of RNA extraction and isolation methods are described in, for example, Doleshal et al., *J. Mol. Diagn.* 10(3): 203-211 (2008), in Peirson et al., *Methods Mol. Biol.* 362: 315-327 (2007), and in Chomcyznski et al., *Nat. Protocols* 1(2): 581-585 (2006), the entire contents of each of which are incorporated herein by reference.

As is evident from the foregoing discussion, the nucleic acid sample extracted from the specimen can be a DNA sample or an RNA sample. In some embodiments, the nucleic acid sample corresponds to genomic DNA extracted from the nucleus of one or more cells such as a tumor infiltrating lymphocyte. In certain embodiments, the nucleic acid sample corresponds to total RNA isolated from one or more cells isolated from the specimen, such as a tumor infiltrating lymphocyte.

While RNA can, in certain circumstances, be more difficult to isolate due to the presence of hardy RNAses in cells which degrade isolated RNA strands, in some embodiments RNA provides certain advantages as a nucleic acid sample. First, the relative abundance of RNA in the isolated cells may reflect more accurately the underlying biology of the T-cells, where the most activated, tumor-specific T-cells may express higher amounts of neoantigen-specific receptor transcripts. For purposes of cloning a therapeutically-effective population of T-cells from co-occurrence information, this inherent mapping of relative T-cell activation to RNA abundance may yield co-occurrence information that can be used to engineer T-cell populations with improved efficacy.

Second, in some embodiments, depending of the portion of the nucleic acid sample that is sequenced, it may be easier to obtain the sequence information from an RNA sample than a corresponding DNA sample. For the segments of the complementarity determining region 3 (CDR3) region that code for the $\alpha$ and $\beta$ chains of T-cell receptors, there is a 5 kb intron between the hypervariable diversity/joining and constant gene that is spliced out in the RNA, which increases the chances of capturing the full receptor coding sequence including the CDR3 region by sequencing RNA rather than genomic DNA. As will be explained in greater detail below, sequencing the CDR3 region can be particularly relevant for identifying co-occurrence of nucleic acid segments that code for functional T-cell receptors.

Obtained from the specimen in step 102 of FIG. 1, the nucleic acid sample includes multiple nucleic acid fragments that are associated with expression of a protein or polypeptide of interest in the specimen. As discussed previously, in some embodiments, the expressed polypeptide is a functional T-cell neoantigen receptor, and in particular, the $\alpha$ and $\beta$ chains of the neoantigen receptor. Accordingly, the nucleic acid fragments correspond to partial or complete coding fragments for the $\alpha$ and $\beta$ chains of the neoantigen receptor.

To begin determining whether two nucleic acid segments co-occur in the nucleic acid sample, the sequences of the two nucleic acid segments within each of the sample fragments are determined in step 104. In general, any two nucleic acid segments within each of the sample's nucleic acid fragments can be tested for co-occurrence. However, certain segments may be more relevant than others in some circumstances.

Nucleic acid sequences that code for portions of the $\alpha$ and $\beta$ chains of the neoantigen receptor can be found in complementarity determining regions 1, 2, and 3 (CDR1, CDR2, CDR3), among others. Among CDR1, CDR2, and CDR3, region CDR3 in particular is hypervariable due to natural VDJ recombination in T-cells and B-cells. In these cells, variable (V), diversity (D), and joining (J) gene segments are randomly assembled to generate unique antigen (or neoantigen) receptors that can recognize different antigens and neoantigens. When the T-cell or B-cell successfully recognizes an antigen or neoantigen, a signal transduction occurs and the gene segments that code for the receptor enter the immunological memory.

Due to hypervariable diversity in the CDR3 region, nucleic acid sequences in this region are almost absolutely unique. In other words, each cell (e.g., T-cell or B-cell) will have a different nucleic acid sequence in this region, which functions as a type of molecular barcode for the cell. Accordingly, by comparing nucleic acid segments within the CDR3 region of nucleic acid fragments, co-occurrence of two particular segments can readily be determined with comparatively little chance of error due to non-uniqueness of segment sequences.

To determine the sequences of the two nucleic acid segments of interest in step 104, a variety of published and commercially-available next-generation sequencing methods can be used. Suitable sequencing methods include, but are not limited to, massively parallel signature sequencing, polony sequencing, 454 sequencing, Illumina sequencing, ion torrent sequencing, SOLiD DNA sequencing technology, and DNA nanoball sequencing. Aspects of suitable sequencing methods are described, for example, in Rajesh et al., *Current Developments in Biotechnology and Bioengineering*, pp. 143-158 (2017), the entire contents of which are incorporated by reference herein.

Sequencing nucleic acid segments of nucleic acid fragments derived from multiple cells yields a distribution of segment sequences, each present at a different frequency in a nucleic acid sample. FIG. 2 is a table showing a portion of a distribution of nucleic acid segment sequences obtained from different nucleic acid fragments in a sample. Each of the sequences in FIG. 2 corresponds to the same portion of different nucleic acid fragments (e.g., a portion of the CDR3 region in multiple fragments) in the sample. The left column of the table shows each of the segment sequences, and the right column shows the frequency of each of the sequences in the nucleic acid sample.

Sequencing the two nucleic acid segments in each of the nucleic acid fragments of the sample yields two sets of sequences: a first set of sequences corresponding to the first nucleic acid segment of each of the fragments, and a second set of sequences corresponding to the second nucleic acid segment of each of the fragments. Within each set of sequences, different sequences are present at different frequencies, with the most common sequences corresponding to most commonly present cells in the specimen.

The number of base pairs in the first nucleic acid segment, in the second nucleic acid segment, or in both the first and second nucleic acid segments, can generally be selected as desired. In some embodiments, for example, the number of base pairs is between 50 and 200 (e.g., between 50 and 190, between 60 and 190, between 60 and 180, between 70 and 180, between 70 and 170, between 70 and 160, between 75 and 150, between 80 and 140, between 80 and 130, between 80 and 120).

The first set of sequences, the second set of sequences, or both the first and second sets of sequences can generally include any number of different sequences, depending upon the number of specimen cells from which the nucleic acid sample is derived. In some embodiments, for example, the number of different sequences is 10 or more (e.g., 12 or more, 15 or more, 20 or more, 30 or more, 40 or more, 45 or more, 48 or more, 50 or more, 60 or more, 70 or more, 80 or more, 90 or more, 100 or more, or even more).

Returning to FIG. 1, in the next step 106, a first set of probes are generated from the first set of sequences determined in step 104. Optionally, step 104 can also include ordering the first set of sequences in order of frequency, with the most frequently occurring sequences earlier. Further still, in certain embodiments, sequences in the first set that occur less frequently relative to other sequences can be eliminated from the first set, so that the first set includes only the N different, most-commonly occurring sequences. N can be, for example, 10 or more (e.g., 20 or more, 25 or more, 30 or more, 35 or more, 40 or more, 45 or more, 48 or more, 50 or more, 60 or more, 70 or more, 80 or more, 90 or more, 100 or more, or even more).

The first set of sequences (optionally restricted to only the N most frequent sequences, as described above) is then used to generate a first set of probes for the specimen. To generate the first set of probes, M different sequences among the different (or N different) sequences of the first set (e.g., the M most abundant sequences in the first set) can be used. M can be equal to or less than N, and in some embodiments, can be 48 or less (e.g., 40 or less, 30 or less, 24 or less, 20 or less, 10 or less).

To generate the first set of probes, a population of oligonucleotides is synthesized for each one of the M different sequences. Each of the oligonucleotides in a given population corresponds to only one of the M different sequences, and is linked to a detection moiety to form a probe. FIG. 3 is a schematic diagram showing a probe, which includes an oligonucleotide 302 linked to a detection moiety 304. Just as oligonucleotide 302 corresponds to only one of the M different sequences, detection moiety 304 also corresponds to only one of the M different sequences. Accordingly, after cycling through each of the M different sequences, M different populations of probes are obtained, such that each probe population corresponds to only one of the M different sequences, and the probes of the population include an oligonucleotide 302 and a detection moiety 304 that are unique to only one of the M different sequences.

In general, the oligonucleotides synthesized for probe generation can correspond to different types of nucleic acids. For example, in some embodiments, the oligonucleotides can include DNA sequences (e.g., DNA sequences that are complementary to each of the M different sequences described above). In certain embodiments, the oligonucleotides can include RNA sequences (e.g., RNA antisense sequences that hybridize to M different RNA transcript sequences). In some embodiments, the oligonucleotides can be synthesized and/or modified nucleic acid-containing species, such as peptide nucleic acids (PNAs) and/or xeno nucleic acids (XNAs).

A variety of different methods can be used to synthesize the oligonucleotides from the M different sequences. Examples of such methods include, but are not limited to phosphoramidite-based methods, H-phosphonate-based methods, and phosphotriester methods. Methods for oligonucleotide and peptide nucleic acid synthesis are described, for example, in Herdewijn, P. (ed.), *Oligonucleotide Synthesis*, Springer (2005), and in Braasch et al., "Synthesis and purification of peptide nucleic acids," *Current Protocols in Nucleic Acid Chemistry*, Chapter 4 (2002), the entire contents of each of which are incorporated by reference herein.

Following synthesis of the oligonucleotide populations, each oligonucleotide 302 is linked to a detection moiety 304 to form a probe. The detection moiety 304 facilitates hybridization detection of each probe. In general, the detection moiety can correspond to a molecular fragment that generates a detectable signal, or alternatively, to a molecular fragment that binds to another fragment that generates a detectable signal. A wide variety of different detection moieties can be used to form the probes described above.

In some embodiments, detection moiety 304 includes biotin or a derivative thereof. Methods for linking biotin and its derivatives to oligonucleotide 302 include, for example, binding biotin substituents to allylamino residues on functionalized oligonucleotides via reaction with N-biotinyl-6-aminocaproic acid N-hydroxysuccinimide ester, extension of RNA with poly(A) polymerase, and reaction of an N-hydroxysulfosuccinimide ester linked to biotin with a primary oligonucleotide amine. Additional methods for linking biotin and derivatives thereof to oligonucleotide 302 are described for example in Cook et al., *Nucleic Acids Res.* 16(9): 4077-4095 (1988), in Moritz et al., *RNA,* 20(3): 421-427 (2014), and in Soukup et al., *Bioconj. Chem.* 6: 135-138 (1995), the entire contents of each of which are incorporated herein by reference.

In certain embodiments, detection moiety 304 includes a hapten. Suitable methods for conjugating haptens to oligonucleotide 302 (which is sometimes referred to as hapten labeling) include phosphoramidite-based methods, as described for example in Luehrsen et al., *J. Histochem. Cytochem.* 48(1): 133-145 (2000), the entire contents of which are incorporated herein by reference.

In some embodiments, detection moiety 304 includes a fluorescent moiety. A wide variety of different fluorescent moieties can be used, including, but not limited to: xanthene-based fluorophores such as fluorescein, rhodamine, Oregon green, eosin, and Texas red; cyanine-based fluorophores such as cyanine, indocarbocyanine, oxacarbocyanine, thiacarbocyanine, and merocyanine; squaraine-based fluorophores, including squaraine rotaxane derivatives; naphthalene-based fluorophores, coumarin-based fluorophores, oxadiazole-based fluorophores, such as pyridyloxazole, nitrobenzoxadiazole, and benzoxadiazole; anthracene-based fluorophores such as anthraquinones, pyrene-based fluorophores; oxazine-based fluorophores such as Nile red, Nile blue, cresyl violet, and malachite green; and tetrapyrrole-based fluorophores such as porphin, phthalocyanine, and bilirubin. Methods for linking fluorophores to oligonucleotide 302 are described for example in Proudnikov et al., *Nucl. Acids Res.* 24(22): 4535-4542 (1996), the entire contents of which are incorporated herein by reference.

In certain embodiments, detection moiety 304 includes at least one chelated metal ion. Probes with chelated metal ions can be detected by liberating the metal ion from the probe, and detecting the liberated ion using mass spectrometry techniques. Suitable types of metal ions include, but are not limited to, lanthanide metal ions. Chelating moieties for such ions can be implemented as one or more metal-chelating groups bound to a polymer backbone. Examples of such chelating moieties and methods for preparing oligonucleotide-metal chelates are described in Majonis et al., *Anal. Chem.* 82(21): 8961-8969 (2010), and in Kwiatskowski et al., *Nucl. Acids. Res.* 22(13): 2604-2611 (1994), the entire contents of which are incorporated herein by reference.

In some embodiments, detection moiety 304 includes a molecular barcode. In general, a molecular barcode is an oligonucleotide having a specific sequence that is unique to a particular population of probes. Each of the probes in a particular population (that corresponds to a single one of the M sequences) includes the same molecular barcode. The molecular barcode is not linked to oligonucleotides in any of the other populations, however. In this manner, the probes of each population contain a common molecular barcode that is unique among the different probe populations.

The oligonucleotide that functions as the molecular barcode can generally be a DNA sequence, an RNA sequence, or a modified nucleic acid sequence such as a peptide nucleic acid sequence. The oligonucleotide can include any number of bases or base pairs (e.g., between 5 and 200, between 10 and 200, between 15 and 200, between 20 and 200, between 20 and 180, between 20 and 150, between 30 and 150, between 40 and 150, between 50 and 150, between 50 and 100, between 10 and 50, between 10 and 40, between 10 and 30, between 20 and 50, 20 between 30 and 50).

In certain embodiments, CODEX® barcodes—each of which corresponds to a unique oligonucleotide sequence—can be linked to oligonucleotide 302 (e.g., at the 3' end of oligonucleotide 302). CODEX® barcodes are available from Akoya Biosciences (Menlo Park, Calif.). Methods for linking these barcodes to oligonucleotides are described for example in Goltsev et al., *Cell* 174(4): 968-981 (2018), and in U.S. Pat. No. 9,909,167, the entire contents of each of which are incorporated herein by reference.

In some embodiments, detection moiety 403 includes a reactive moiety that generates chemiluminescence. Specifically, the reactive moiety reacts with a second substance, introduced during a detection step, to generate luminescence that can be detected to identify the presence of the probe. A wide variety of different reactive moieties can be linked to oligonucleotide 302 to generate a chemiluminescent probe. Examples of such reactive moieties include, but are not limited to, luminol and derivatives thereof. Horseradish peroxidase (HRP) catalyzes the conversion of luminol to 3-aminophthalate. When performed in the presence of an enhancer, chemiluminescence is readily observed and permits detection of extremely low probe concentrations. Methods for linking reactive moieties for chemiluminescence detection to oligonucleotides are described, for example, in Khan et al., *Appl. Biochem. Biotechnol.* 173(2): 333-355 (2014), the entire contents of which are incorporated herein by reference.

The M probe populations generated as described above form a first set of probes that correspond to the first nucleic acid segment. Following generation of the first set of probes, a second set of probes is generated in step 108 that correspond to the second nucleic acid fragment. Methods for generating the second set of probes in step 108 can generally correspond to any of the methods described above for forming the first set of probes in step 106, and therefore are not repeated. After completion of step 108, a first set of probes corresponding to the first nucleic acid segment (e.g., a segment that codes for a portion of an α-chain of a T-cell receptor) and a second set of probes corresponding to the second nucleic acid segment (e.g., a segment that codes for a portion of a β-chain of a T-cell receptor) have been generated.

Next, in step 110, a detection sample is exposed to one or more members of the first and second sets of probes. Exposure to the probe sets can be performed in different ways, depending upon the nature of the hybridization analysis that is subsequently performed to determine which of the probes hybridize to the detection sample.

In some embodiments, the detection sample is exposed to the probes in a "pairwise" manner. The detection sample is exposed to a population of probes corresponding to one of the M sequences for the first nucleic acid segment, and to a population of probes corresponding to one of the M sequences for the second nucleic acid segment. Thus, the sample is exposed to only two different types of probes at once (e.g., one corresponding to an α-chain coding fragment and one corresponding to a β-chain coding fragment). Following the hybridization analysis (discussed further below), the two different types of probes are either removed from (e.g., via dehybridization) or quenched in the detection sample and the detection sample is re-used by exposing the detection sample to another pair of different probe populations corresponding to the first and second nucleic acid segments respectively, or a new detection sample is obtained and exposed to the next pair of probe populations. The pairwise exposure cycle is repeated until all pairwise combinations of the probe populations corresponding to the first and second nucleic acid segments have been hybridized and analyzed.

In certain embodiments, the detection sample is exposed to the probes in a "serial" manner. That is, the detection sample is exposed to a population of only one type of probes, corresponding to one of the M sequences for either the first nucleic acid segment or the second nucleic acid segment. Thus, the sample is exposed to only one type of probe at once. Following hybridization analysis, the type of probe is either removed from (e.g., via dehybridization) or quenched in the detection sample and the detection sample is re-used by exposing the detection sample to another single probe population corresponding to one of the first and second nucleic acid segments, or a new detection sample is obtained and exposed to the next one of the probe populations. The single population exposure cycle is repeated until all probe populations corresponding to the first and second nucleic acid segments have been individually hybridized and analyzed.

In some embodiments, the detection sample is exposed to the probes in a "pooled" manner. In other words, the detection sample is exposed to populations of more than one type of probes corresponding to the more than one of the M sequences for the first nucleic acid segment, and/or populations of more than one type of probes corresponding to more than one of the M sequences for the second nucleic acid segment. Following hybridization analysis, the probes are removed from (e.g., via dehybridization) or quenched in the detection sample and a new combination of different types of probes is used to expose the detection sample. Alternatively, a new detection sample can be obtained and exposed to the new combination of different types of probes. The exposure cycles are repeated until the one or more detection samples have been exposed to all combinations of the different probe types corresponding to the first and second nucleic acid segments, so that co-occurrence can be identified for each pair of different sequences corresponding to the first and second nucleic acid segments.

In some embodiments, the detection sample is exposed to the first and second sets of probes in a fully pooled manner. In other words, populations of each of the different types of probes corresponding to the first and second nucleic acid segments are combined and hybridized to the detection sample simultaneously. By using a fully pooled exposure strategy, only a single hybridization cycle is used to evaluate co-occurrence of all pairs of nucleic acid segment sequences, resulting in a considerable simplification of the workflow and corresponding reduction in assay time.

The detection sample is generally obtained from the same specimen as the nucleic acid sample described in step 102. In some embodiments, the detection sample corresponds to a remaining portion of a sample (e.g., a FFPE tissue section) from which the nucleic acid sample has been excised using a technique such as laser capture microdissection. In certain embodiments, the detection sample corresponds to a separate tissue section obtained from the specimen, and can be a fresh section, a fresh-frozen section, or a FFPE tissue section.

Alternatively, in some embodiments, the detection sample is a smear of cells obtained from a body fluid. As an example, the detection sample can correspond to a blood smear mounted on a substrate and including white blood cells (e.g., peripheral blood mononuclear cells).

Returning to FIG. 1, interleaved with the exposure step in step 110, a hybridization analysis is performed in step 112 to determine which of the different types of probes hybridize to the detection sample. In general, the first step in the hybridization analysis includes washing away unhybridized probes from the detection sample, so that such probes do not generate measurement signals. After this washing step, the nature of the hybridization analysis depends upon the nature of the detection moieties that are present in the probes.

The hybridization analysis determines which of the probes to which the detection sample was exposed hybridized to the detection sample. Accordingly, the hybridization analysis involves detecting the hybridized detection probes, and more specifically, detecting the detection moieties of the hybridized detection probes. The method by which the detection moieties are detected depends upon the nature of the detection moieties.

As discussed above, in some embodiments, detection moiety 304 is directly detectable. For example, where detection moiety 304 includes a fluorescent moiety, probes hybridized to the detection sample can be detected directly by measuring fluorescent emission from the detection sample, as will be discussed in greater detail below. Where detection moiety 304 includes a chelated metal ion, probes hybridized to the detection sample can be detected directly by liberating the metal ion, and detecting the metal ion using mass spectrometry techniques. Methods for mass spectrometry-based detection of metal ion-labeled samples are described for example in Keren et al., "MIBI-TOF: A multiplexed imaging platform relates cellular phenotypes and tissue structure," *Sci. Adv.* 5(10): eaax5851 (2019), and in Angelo et al., *Nat. Medicine* 20: 436-442 (2014), the entire contents of each of which are incorporated by reference herein.

In contrast, in certain embodiments, detection moiety 304 is not directly detectable, and a detection probe is conjugated to detection moiety 304 to permit probe hybridization to be detected. FIG. 4 is a schematic diagram showing an example structure of a detection probe 400. Probe 400 includes a binding group 402 and a label 404. In general, label 404 includes a fluorescent moiety that generates fluorescence emission, which is detected to identify probe hybridization to the detection sample. Any of the fluorescent moieties and their derivatives discussed above can generally be used in label 404.

The nature of binding group 402 depends on the nature of the probe detection moiety 304. In embodiments where detection moiety 304 includes biotin or a derivative thereof, binding group can include a moiety that binds to biotin or a derivative thereof. Examples of such moieties include, but are not limited to, an avidin- or streptavidin-based binding group that conjugates biotin to link detection probe 400 to detection moiety 304.

In embodiments where detection moiety 304 includes a hapten, binding group 402 can include a moiety that binds to the hapten. Examples of suitable moieties include, but are not limited to, proteins, polypeptides, polysaccharides, and liposomes.

In embodiments where detection moiety 304 includes a reactive moiety that generates chemiluminescence, the probe detection moiety 304 is typically not conjugated to a detection probe 400. Instead, detection moiety 304 is exposed to an agent that reacts with the reactive moiety, generating detectable chemiluminescence in the detection sample. A variety of different agents can be used, depending upon the nature of the reactive moiety. For example, where the reactive moiety is luminol-based, the agent can include an enzyme such as horseradish peroxidase that reacts with luminol to generate chemiluminescence.

In embodiments where detection moiety 304 is an oligonucleotide such as a molecular barcode, binding group 402 can be an oligonucleotide that is at least partially complementary with detection moiety 304, and hybridizes to detection moiety 304. The extent of complementarity between detection moiety 304 and binding group 402 can be 70% or more (e.g., 80% or more, 85% or more, 90% or more, 95% or more, 97% or more, 99% or more, or even 100%).

In embodiments where detection moiety 304 is a CODEX® barcode (obtained from Akoya Biosciences), detection probe 400 can correspond to a complementary CODEX® Reporter consisting of a dye-labeled reporter sequence. Hybridization of the CODEX® Reporter to the detection moiety 304 yields a conjugate probe structure from which fluorescence emission can be detected to identify hybridization of specific probes to the detection sample.

In addition to CODEX® Reporters, detection probe 400 can correspond more generally to a wide variety of fluorescence in-situ hybridization (FISH) probes. Such probes generally include an oligonucleotide binding group 402, and a conjugated fluorophore. Measurement of fluorescence emission from the fluorophore reveals hybridization of a probe conjugated to a corresponding FISH probe. In certain embodiments, FISH detection probes can include a detection probe 400 that includes an oligonucleotide binding group 402 and a multiplicity of coupling groups. Suitable coupling groups include, for example, antigens. After the FISH detection probe has hybridized to the detection moiety 304, multiple amplification probes each consisting of a fluorophore conjugated to complementary coupling group are introduced and bound to the FISH detection probe. Suitable complementary coupling groups include antibodies, for example. In this manner, an amplified FISH detection probe can be hybridized to a sample-hybridized nucleic acid segment probe, increasing the intensity of fluorescence emission that is indicative of hybridization of the nucleic acid segment probe.

The nucleic acid character of binding group 402 depends on the nucleic acid character of detection moiety 304. For example, when detection moiety 304 is an oligonucleotide with a double-stranded DNA sequence, binding group 402 corresponds to a complementary single-stranded DNA sequence. Detection moiety 304 can be denatured prior to hybridization of binding group 402 to one of the double strands of detection moiety 304. When detection moiety 304 is a single-stranded DNA sequence, hybridization of binding group 402 can be directly performed. When detection moiety 304 is an oligonucleotide with an RNA sequence, binding group 402 corresponds to an antisense RNA sequence that is complementary to at least a portion of the RNA sequence.

As described above, when detection moiety 304 reacts to yield chemiluminescence, or when detection moiety 304 includes (or is linked to a detection probe 400 that includes) a fluorescent moiety, light emission from the detection sample is measured to determine which probes are hybridized to the detection sample. FIG. 5 shows a schematic diagram of a system 500 for detecting light emission (e.g., chemiluminescence, fluorescence emission) from a detection sample. System 500 includes a light source 502, an optical assembly 504, a stage 506 supporting a detection sample 508, a wavelength-dependent reflection element 510, a filter assembly 512, and a detector 514. To detect chemiluminescence from detection sample 508, light source 502, reflection element 510, and filter assembly 512 can optionally be omitted from system 500.

Detector 514 is an imaging detector such as a CCD detector, and obtains one or more images of light emitted from detection sample 514. Chemiluminescence is generated directly by probes in the detection sample and imaged by detector 514. To measure fluorescence from probes in the detection sample, light source 502 (e.g., a multi-diode array) generates excitation light in a selected wavelength band that passes through reflective element 510 and is directed by optical assembly 504 onto detection sample 508. The excitation light stimulates fluorescence emission from hybridized probes in detection sample 508, and the emitted fluorescence is reflected by reflective element 510, passes through filter assembly 512, and is detected by detector 514. Note that in the following discussion, fluorescence measurement is discussed by way of example, but it should be understood that the methods described apply equally to detection of probe hybridization in the detection sample by measurement of chemiluminescence.

The nature of image acquisition by detector 514 depends on the nature of the hybridization analysis in step 112. In general, images of fluorescence emission in a single wavelength band or in multiple wavelength bands can be acquired by system 500. In some embodiments, where the serial probe exposure strategy is used as discussed above, and optionally where paired or pooled probe exposure strategies are used, detection sample images showing fluorescence emission in a single wavelength band are acquired. Thus, for example, in a paired exposure strategy with different fluorescent labels attached to each of two different types of probes hybridized to the sample, two fluorescence images of the sample are obtained, each image corresponding to fluorescence emission in a different wavelength band associated with one of the fluorescent labels. For a pooled probe exposure strategy in which Q different fluorescent labels are each attached to one of Q different and corresponding hybridized sample probe types, Q fluorescence images of the detection sample are obtained, each of the Q images corresponding to emission from a different one of the Q probe types.

In certain embodiments, where paired or pooled exposure strategies are used so that the detection sample includes multiple different types of hybridized probes, multi-band fluorescence images can be obtained showing fluorescence emission in multiple spectral bands, each corresponding to emission from a different one of the unique fluorescent labels attached to the different types of probes.

In some embodiments, as discussed above, the probes in each population can include a detection moiety 304 that corresponds to a molecular barcode such as a CODEX® barcode, and the probe populations can be pooled to form a composition that includes probes corresponding to all of the sequences corresponding to the first and second nucleic acid segments. The fully pooled probes can then be simultaneously hybridized to the detection sample in a single hybridization step. To facilitate probe hybridization detection when the probe detection moieties correspond to CODEX® barcodes, CODEX® Reporters can be used in multiplexed fashion to perform multiple detection cycles, each of which yields a sample fluorescence image in which emission from multiple CODEX® Reporters is measured.

For example, in a first detection cycle, multiple (e.g., 3, 4, 5, or even more; generally k) CODEX® Reporters are hybridized to k nucleic acid segment probes hybridized to the detection sample. A fluorescence image of the detection sample is obtained showing fluorescence emission in k different spectral bands, each of which corresponds to a different one of the k CODEX® Reporters, and therefore, to a different one of the hybridized nucleic acid segment probes. After imaging, the k CODEX® Reporters are washed out of the detection sample, and new analysis cycle in which a new set of k different CODEX® Reporters is hybridized to a different set of k nucleic acid segment probes hybridized to the detection sample begins. Another fluorescence image showing emission in k different spectral bands, each corresponding to a different one of the new set of k nucleic acid segment probes is obtained, before the new set of k CODEX® Reporters is washed out of the detection sample. The CODEX® hybridize-image-wash cycles continue until hybridization of each of the different probe types in the detection sample is analyzed.

For each different type of probe, the extent of hybridization of the probe to the detection sample is determined by the presence of fluorescence emission corresponding to the probe in a sample image. If the probe exhibits no fluorescence emission, then the probe did not hybridize to the detection sample (and was presumably washed out of the sample prior to imaging). If the probe exhibits fluorescence emission in a sample image, then the probe is hybridized to the sample. Since each type of probe is associated with one of the sequences corresponding to either the first or second nucleic acid segment, hybridization of a particular type of probe to the detection sample indicates that the nucleic acid segment corresponding to the sequence associated with the hybridized probe occurs in the detection sample. Thus, by imaging fluorescence emission from each of the different types of probes, the occurrence of each type of nucleic acid segment sequence in the detection sample can be assessed.

It should be further noted that while the foregoing and subsequent discussion involves fluorescence measurements for identifying nucleic acid segment occurrence in a sample, other methods as described herein (e.g., detection of liberated metal ions, chemiluminescence) can also be used, as the analytical workflow is analogous for non-fluorescence images.

Returning to FIG. 1, once the hybridization of different probes to the detection sample has been determined and the occurrence of specific nucleic acid segment sequences has been identified, co-occurrence of specific nucleic acid segments in a single cell can be determined. In general, for a particular sample cell, two specific nucleic acid segments co-occur in the sample cell if the fluorescence emission corresponding to the two nucleic acid segments is co-localized in sample fluorescence images. Co-location is readily identified if a fluorescence image shows emission corresponding to both of the two nucleic acid segments in the same image, as the fluorescence emission will arise from a common spatial location in the image.

For example, FIG. 6A is a schematic fluorescence image showing fluorescence emission corresponding to two different nucleic acid segment probes. At locations 602 and 604 in the image, fluorescence emission corresponding to each of the nucleic acid segment probes is observed. Accordingly, the nucleic acid segments co-occur in the cells at locations 602 and 604 in the sample, but not in the other sample cells.

Where the fluorescence emission from the two nucleic acid segments is shown in different sample images, the spatial locations of the fluorescence emission in the different sample images is measured. If the spatial locations in the different images correspond to within an error threshold for the assay, the two nucleic acid segments are deemed to co-occur in cell. If the difference in spatial locations is too large, the two nucleic acid segments do not co-occur in the cell.

As an example, FIG. 6B shows two schematic fluorescence images, each of which shows fluorescence emission corresponding to a different nucleic acid segment probe hybridized to a sample. At most of the locations in the two images, no fluorescence emission is observed, or fluorescence emission corresponding to only one of the nucleic acid segment probes is observed. However, at location 606 in left image, fluorescence emission corresponding to the first nucleic acid segment probe is observed, and at location 606 in the right image, fluorescence emission corresponding to the second nucleic acid segment probe is observed. Accordingly, the two nucleic acid segments co-occur in the cell at location 606 in the sample, but not in the other sample cells.

Once the sample fluorescence images have been obtained, the foregoing analysis can be rapidly applied to determine which pairs of nucleic acid segments co-occur in each of multiple sample cells. For a specimen in which the first and second nucleic acid segments correspond to coding sequences for α- and ß-chains of a functional T-cell, the co-occurrence information reveals which combinations of coding sequences for the α- and ß-chains may yield functional T-cells. This information can then be used to engineer specific T-cell clonal populations for targeted immunotherapies.

Applications

Information about co-occurrence of nucleic acid segments can be used for a variety of different therapeutic applications, and in particular, for synthesis of therapeutics that are delivered to a patient. As mentioned above, the development of therapies for treating solid tumor malignancies has not been as rapid as the development of therapies for hematic malignancies, due in part to the absence of reliable biomarkers. However, solid tumor cells produce neoantigens which are recognized by surface neoantigen receptors of functional T-cells. Accordingly, co-occurrence information for nucleic acid segments that correspond to α- and ß-chains of neoantigen receptors of functional T-cells can be used to engineer populations of the functional T-cells, which can then be therapeutically administered to a patient.

A variety of different methods for T-cell engineering that use the co-occurrence information obtained as described herein can be used to prepare therapeutic functional T-cell populations. Examples of such methods are described, for instance, in Li et al., *Signal Transduction and Targeted Therapy* 4: 35 (2019), the entire contents of which are incorporated by reference herein.

Information about co-occurrence of nucleic acid segments can also be used for targeted B-cell engineering as part of a therapeutic program. In particular, co-occurrence information for nucleic acid segments that code for heavy and light chain fragments of B-cell receptors can be used to identify functional B-cells. Populations of therapeutic B-cells can then be engineered and delivered to a patient. Suitable methods for B-cell engineering of therapeutic B-cell lines are described, for example, in Moffett et al., *Science Immunology* 4(35): eaax0644 (2019), in Wu et al., *J. Immunol. Methods* 457: 33-40 (2018), and in Johnson et al., *Sci.*

Other Embodiments

While this disclosure describes specific implementations, these should not be construed as limitations on the scope of the disclosure, but rather as descriptions of features in certain embodiments. Features that are described in the context of separate embodiments can also generally be implemented in combination in a single embodiment. Conversely, various features that are described in the context of a single embodiment can also be implemented in multiple embodiments separately or in any suitable sub-combination. Moreover, although features may be described above as present in certain combinations and even initially claimed as such, one or more features from a claimed combination can generally be excised from the combination, and the claimed combination may be directed to a sub-combination or variation of a sub-combination.

In addition to the embodiments expressly disclosed herein, it will be understood that various modifications to the embodiments described may be made without departing from the spirit and scope of the disclosure. Accordingly, other embodiments are within the scope of the following claims.

What is claimed is:

1. A method for identifying co-occurrence of nucleic acid segments in a nucleic acid sample from a specimen, the method comprising:
obtaining a nucleic acid sample from a specimen, wherein the nucleic acid sample comprises a plurality of nucleic acid fragments that code for an antigen receptor molecule in the specimen;
determining sequences of first and second nucleic acid segments in the nucleic acid fragments of the sample to generate a first set of sequences corresponding to the first nucleic acid segment and a second set of sequences corresponding to the second nucleic acid in the sample;
generating a first set of probes from the first set of sequences, wherein each member of the first set of probes comprises an oligonucleotide corresponding to a different one of the first set of sequences linked to a detection moiety;
generating a second set of probes from the second set of sequences, wherein each member of the second set of probes comprises an oligonucleotide corresponding to a different one of the second set of sequences linked to a detection moiety;
exposing a detection sample obtained from the specimen to a member of the first set of probes and a member of the second set of probes;
performing a hybridization analysis to determine whether the member of the first set of probes hybridizes to the detection sample, and to determine whether the member of the second set of probes hybridizes to the detection sample; and
determining whether the first and second nucleic acid segments co-occur in a same cell of the specimen.

2. The method of claim 1, wherein the first nucleic acid segment is associated with an α-chain of a T-cell antigen receptor molecule, and wherein the second nucleic acid segment is associated with a β-chain of the T-cell antigen receptor molecule.

3. The method of claim 1, wherein the first nucleic acid segment is associated with a heavy chain of a B-cell antigen receptor molecule, and wherein the second nucleic acid segment is associated with a light chain of the B-cell antigen receptor molecule.

4. The method of claim 2, wherein the first and second nucleic acid segments are located in a complementarity determining region 3 (CDR3) portion of the nucleic acid fragments.

5. The method of claim 1, wherein the nucleic acid sample comprises one member selected from the group consisting of genomic DNA and total RNA.

6. The method of claim 1, wherein the nucleic acid sample comprises nucleic acid molecules from tumor infiltrating lymphocytes.

7. The method of claim 1, wherein obtaining the nucleic acid sample from the specimen comprises:
fixing and embedding the specimen in paraffin;
excising a portion of the specimen; and
extracting the nucleic acid sample from the excised portion of the specimen.

8. The method of claim 1, wherein the first set of sequences comprises N different sequences, and wherein generating the first set of probes comprises:
for each sequence of M of the different sequences that are expressed in highest abundance in the nucleic acid sample, generating a population of oligonucleotides corresponding to the sequence; and
linking each member of the population of oligonucleotides to a detection moiety.

9. The method of claim 8, wherein M is 48 or less.

10. The method of claim 8, wherein the oligonucleotides of the population comprise DNA sequences that are complementary to the M different sequences.

11. The method of claim 8, wherein the oligonucleotides of the population comprise RNA sequences that are complementary to RNA transcript sequences corresponding to the M different sequences.

12. The method of claim 8, wherein the oligonucleotides of the population comprise peptide nucleic acids.

13. The method of claim 8, wherein the detection moiety comprises at least one member selected from the group consisting of biotin and derivatives thereof, or a hapten.

14. The method of claim 8, wherein the detection moiety comprises a fluorescent moiety.

15. The method of claim 8, wherein the detection moiety comprises at least one chelated metal ion.

16. The method of claim 8, wherein the detection moiety comprises a molecular barcode comprising an oligonucleotide, and wherein each member of the population is linked to a common detection moiety comprising the same molecular barcode.

17. The method of claim 16, wherein among the populations of nucleotides corresponding to the M different sequences, the common detection moiety is unique to one population of oligonucleotides corresponding to only one of the M different sequences.

18. The method of claim 8, wherein the detection moiety comprises a reactive moiety that reacts with an agent to generate chemiluminescence.

19. The method of claim 1, wherein the detection sample comprises a formalin fixed, paraffin embedded tissue section.

20. The method of claim 19, wherein the detection sample comprises a remaining portion of the specimen following extraction of a portion of the specimen to obtain the nucleic acid sample.

21. The method of claim 1, wherein the detection sample comprises a smear of white blood cells comprising peripheral blood mononuclear cells (PBMCs).

22. The method of claim 1, wherein exposing the detection sample to the members of the first and second sets of probes comprises:
contacting the detection sample with a composition comprising all members of the first and second sets of probes; and
removing members of the first and second sets of probes that do not hybridize to the detection sample from contact with the detection sample.

23. The method of claim 22, wherein:
the first set of probes comprises J different types of probes, each of the J different types of probes corresponding to one of the first set of sequences;
the second set of probes comprises K different types of probes, each of the K different types of probes corresponding to one of the second set of sequences;
each member of the first and second sets of probes corresponds to only one of the J different types of probes or to only one of the K different types of probes;
each member of the first and second sets of probes comprises a detection moiety comprising a molecular barcode that is unique to only one type of probe among the J and K different types of probes; and
the molecular barcode comprises an oligonucleotide.

24. The method of claim 23, wherein performing the hybridization analysis comprises:
(a) exposing the detection sample to a set of detection probes, each member of the set of detection probes comprising an oligonucleotide sequence that hybridizes to a single type of molecular barcode, and a fluorescent moiety linked to the oligonucleotide sequence;
(b) detecting fluorescence emission from members of the set of detection probes hybridized to molecular barcodes in the detection sample;
(c) removing from the detection sample the detection probes that are hybridized to molecular barcodes in the sample; and
(d) repeating steps (a)-(c) with additional sets of detection probes.

25. The method of claim 1, wherein:
the first set of probes comprises J different types of probes, each of the J different types of probes corresponding to one of the first set of sequences;
the second set of probes comprises K different types of probes, each of the K different types of probes corresponding to one of the second set of sequences; and
exposing the detection sample to the members of the first and second sets of probes comprises contacting the detection sample with a composition comprising one of the J different types of probes and one of the K different types of probes, and removing from contact with the detection sample any probes of the composition that do not hybridize to the detection sample.

26. The method of claim 25, wherein performing the hybridization analysis comprises detecting the detection moiety linked to the one of the J different types of probes and detecting the detection moiety linked to the one of the K different types of probes.

27. The method of claim 26, wherein the detection moiety linked to the one of the J different types of probes comprises biotin or a derivative thereof, and wherein detecting the detection moiety comprises:
binding the detection moiety to a detection probe, the detection probe comprising a moiety that binds to biotin or a derivative thereof and a fluorescent moiety; and
detecting fluorescence emission from the fluorescent moiety following binding of the detection moiety to the detection probe.

28. The method of claim 27, wherein the moiety that binds to biotin or a derivative thereof comprises at least one of avidin and streptavidin.

29. The method of claim 26, wherein the detection moiety linked to the one of the J different types of probes comprises a hapten, and wherein detecting the detection moiety comprises:
binding the detection moiety to a detection probe, the detection probe comprising a moiety that binds to the hapten and a fluorescent moiety; and
detecting fluorescence emission from the fluorescent moiety following binding of the detection moiety to the detection probe.

30. The method of claim 29, wherein the moiety that binds to the hapten comprises at least one member selected from the group consisting of a protein, a polypeptide, a polysaccharide, or a liposome.

31. The method of claim 26, wherein the detection moiety linked to the one of the J different types of probes comprises a fluorescent moiety, and wherein detecting the detection moiety comprises detecting fluorescence emission from the fluorescent moiety.

32. The method of claim 26, wherein the detection moiety linked to the one of the J different types of probes comprises at least one chelated metal ion, and wherein detecting the detection moiety comprises:
liberating the chelated metal ion from the detection moiety; and
detecting the liberated metal ion by mass spectrometry.

33. The method of claim 26, wherein the detection moiety linked to the one of the J different types of probes comprises a reactive group, and wherein detecting the detection moiety comprises:
exposing the reactive group to an agent that reacts with the reactive group to generate chemiluminescence emission; and
detecting the chemiluminescence emission following the reaction.

* * * * *

SEQUENCE LISTING

```
<160> NUMBER OF SEQ ID NOS: 8

<210> SEQ ID NO 1
<211> LENGTH: 51
<212> TYPE: DNA
<213> ORGANISM: Homo sapiens

<400> SEQUENCE: 1
tgtgccagca gcccggcgac tagcgggaga atcatcgatg agcagttctt c          51

<210> SEQ ID NO 2
<211> LENGTH: 51
<212> TYPE: DNA
<213> ORGANISM: Homo sapiens

<400> SEQUENCE: 2
tgtgctaccc aacttctgag ggaattgagc tcctacaatg agcagttctt c          51

<210> SEQ ID NO 3
<211> LENGTH: 57
<212> TYPE: DNA
<213> ORGANISM: Homo sapiens

<400> SEQUENCE: 3
tgtgccagta gtaccccct actagagcgg gagaggtaca ccggggagct gtttttt     57

<210> SEQ ID NO 4
<211> LENGTH: 42
<212> TYPE: DNA
<213> ORGANISM: Homo sapiens

<400> SEQUENCE: 4
tgtgccagca ggcagcctgg aggggatca cccctccact tt                    42

<210> SEQ ID NO 5
<211> LENGTH: 39
<212> TYPE: DNA
<213> ORGANISM: Homo sapiens

<400> SEQUENCE: 5
tgcagtgcta ggtttcaggc aaatcagccc cagcatttt                       39

<210> SEQ ID NO 6
<211> LENGTH: 36
<212> TYPE: DNA
<213> ORGANISM: Homo sapiens

<400> SEQUENCE: 6
tgtgccagcg gcgggcacgg ttgtttcata tatttt                          36
```

```
<210> SEQ ID NO 7
<211> LENGTH: 42
<212> TYPE: DNA
<213> ORGANISM: Homo sapiens

<400> SEQUENCE: 7
tgtgccagca ggcagcctgg agagggatca cccctccact tt                              42

<210> SEQ ID NO 8
<211> LENGTH: 38
<212> TYPE: DNA
<213> ORGANISM: Homo sapiens

<400> SEQUENCE: 8
tgagtgctag gtttcaggca aatcagcccc agcatttt                                   38
```